United States Patent [19]

Drits

[11] Patent Number: 5,059,905

[45] Date of Patent: Oct. 22, 1991

[54] INDICATION OF CUTTING TOOL WEAR BY MONITORING EDDY CURRENTS INDUCED IN A METALLIC WORKPIECE

[75] Inventor: Vladimir Drits, Minnetonka, Minn.

[73] Assignee: Innovex Inc., Hopkins, Minn.

[21] Appl. No.: 399,324

[22] Filed: Aug. 28, 1989

[51] Int. Cl.$^5$ .................. G01N 27/80; G01N 27/90; G01R 33/12

[52] U.S. Cl. .................. 324/233; 73/104; 324/202; 324/222; 324/226; 324/227; 324/232; 324/238

[58] Field of Search .............. 324/202, 222, 223, 224, 324/226, 227, 232, 233, 234, 236–243, 207.16, 207.26; 73/104, 105; 340/680

[56] References Cited

U.S. PATENT DOCUMENTS

| | | | |
|---|---|---|---|
| 3,889,520 | 6/1975 | Stöferle | 73/37.5 |
| 3,939,404 | 2/1976 | Tait | 324/224 |
| 4,000,459 | 12/1976 | Little | 324/207.26 |
| 4,112,365 | 9/1978 | Larson et al. | 324/207.16 X |
| 4,333,052 | 1/1982 | Schmall | 324/207.26 |
| 4,387,338 | 1/1983 | Hecht et al. | 324/236 |
| 4,460,869 | 7/1984 | Buser et al. | 324/227 X |
| 4,563,987 | 1/1986 | Moore | 73/587 |
| 4,620,281 | 10/1986 | Thompson et al. | 73/104 |
| 4,644,335 | 2/1987 | Wen | 340/683 |
| 4,854,161 | 8/1989 | Drits | 73/104 |

OTHER PUBLICATIONS

"New Tool-Wear Sensors Aid Adaptive Machining", Joseph C. Quinlan, Dec. 1987, *Tooling & Production*, pp. 41–43.

"Measuring Cutting Tool Wear On-Line: Some Practical Considerations", Jul. 1984, *Manufacturing Engineering*, pp. 55–60.

*Primary Examiner*—Gerard R. Strecker
*Attorney, Agent, or Firm*—Kinney & Lange

[57] ABSTRACT

A tool dullness indicator and method comprising the measurement of eddy currents at a known, controlled frequency directly in the tool by measuring the phase angle shift in a coil when a sample is put into or next to the coil. The phase angle change caused by presence of a workpiece is measured when the tool is sharp to provide a reference reading taking into account the surface hardness and other bulk properties of the workpiece, and arriving at a parameter that is dependent on eddy current changes, such as phase angle shift or other measurable changes related to eddy currents in the part, and then analyzing the workpiece, either while working, or at a set programmed check time to determine when the tool is dull as a function of the change in eddy current characteristics caused by work hardening.

12 Claims, 2 Drawing Sheets

INDICATION OF CUTTING TOOL WEAR BY MONITORING EDDY CURRENTS INDUCED IN A METALLIC WORKPIECE

BACKGROUND OF THE INVENTION

1. Field of the Invention

The present invention relates to apparatus and methods for determining cutting tool dullness by analyzing surface conditions on a workpiece.

2. Description of the Prior Art

In both automatic and manual machine operations, it is important to know the degree of wear or dullness of the cutting tool. Different methods of attempting to monitor cutting tool dullness have been advanced, and tool wear sensors that provide on-line measurements have long been sought after. Some current methods are disclosed in articles entitled, "Measuring Cutting Tool Wear On-Line: Some Practical Considerations", *Manufacturing Engineering*, July 1984, pages 55-60; and "New Tool-Wear Sensors Aid Adaptive Machining", *Tooling and Precision*. December 1987, pages 41-43. The methods disclosed in these articles are characterized as being either direct or indirect methods. Indirect methods include force measurement, temperature measurement, vibration measurement, and sound measurement techniques. Present direct methods use workpiece size change, radiometric, tool/work junction electrical resistance and optical monitoring.

Addition art that shows apparatus for monitoring various cutting tool conditions is shown in U.S. Pat. No. 4,644,335 which provides information by way of acoustic signature; Pat. No. 3,889,520 which provides a fluidic system for monitoring machine tool wear resulting in a change in gap between the nozzle and the workpiece as the cutting tool wears; and U.S. Pat. No. 4,563,897 which is based upon a vibration value that is compared to a stored parameter.

The prior art generally is used for detecting breaks in tools which gives sharp spike in output signal. It has been long desired to have an on-line device which was reliable and accurate.

U.S Pat. No. 4,854,161 shows a method of diagnosing cutting tool dullness which utilizes two known parameters and measures these parameters and then provides values based on the two parameters and characterizes the tool if the known value is greater than the threshold. This, however, does involve making two measurements and comparing the results.

SUMMARY OF THE INVENTION

The present invention relates to an apparatus and method for directly measuring a surface condition of a work piece which varies with tool dullness. The condition is related to the effect on eddy currents caused by work hardening of the workpiece surface. The apparatus comprises an eddy current generator or probe, either adjacent or around the workpiece, and having means for determining a change in a parameter related to the eddy current changes which occur as the cutting tool gets dull. The selected parameter that is a function of eddy currents in the workpiece is monitored or checked from time to time and changes in this parameter are correlated as an indication of tool dullness. The parameter preferably measured is the phase shift of the input current as the tool becomes dull. The eddy current generator preferably has a frequency in the range of 1,000 Hz, in order to provide for a straight line function between phase shift and tool dullness. Very high frequency currents from the eddy current generator provide unstable results, and not a clearly defined relationship.

The parameter to be measured preferably is the phase shift of the current through a coil or coils in a probe used as the eddy current generator.

Separate coils can be used adjacent to the workpiece in a position where the work piece is affected by the magnetic field of the coils or probe when alternating currents are used. A shift in the phase of the current in the coil or probe results as the work piece surface work hardens and this shift will be different for different degrees of cutting tool dullness.

DETAILED DESCRIPTION OF THE PREFERRED EMBODIMENTS

The change in work hardening of machined surfaces is a good criteria to diagnose the level of wear in cutting tools, and this has been recognized for years. However, direct measurements using prior art methods have been less than reliable. The present invention indicates that when eddy currents are sensed at frequencies not substantially above one KHz a straight line relationship between tool dullness and input current phase change can be observed in work parts of the same material.

Figure 1:
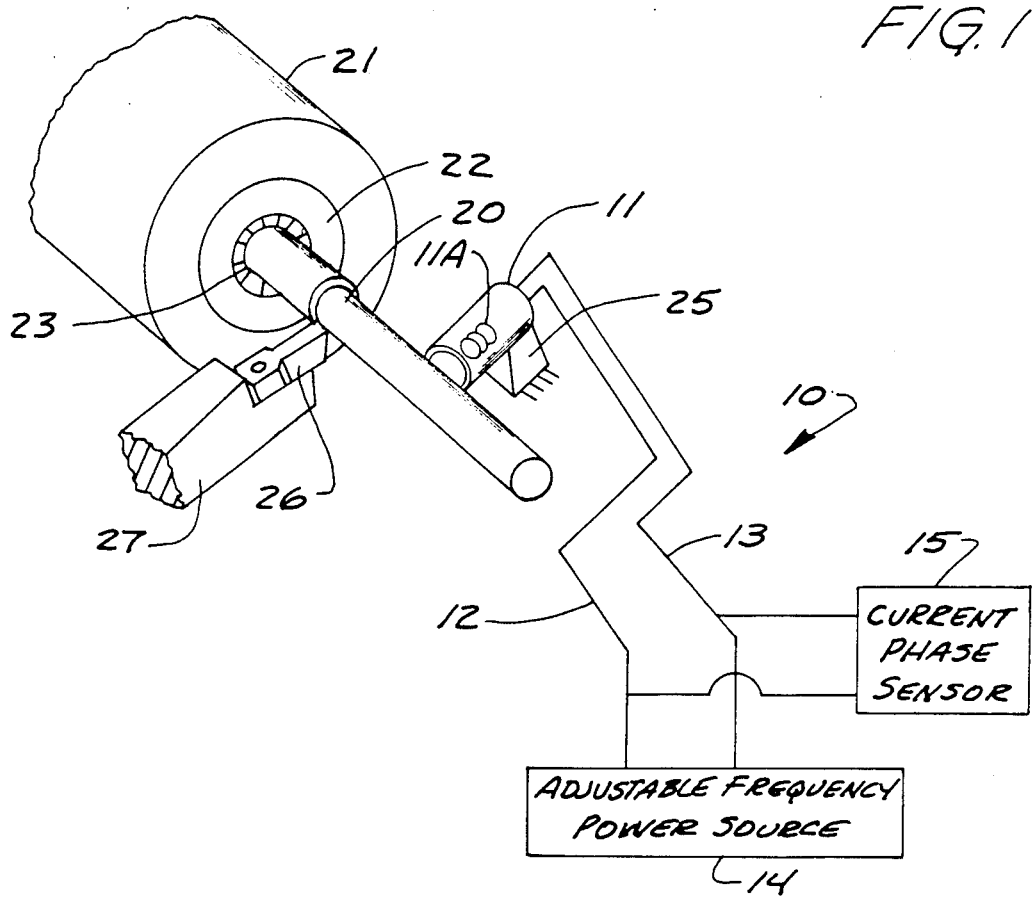
FIG. 1 is a schematic representation of a machine tool driving a piece part, and showing a cutting tool in place, together with a probe for generating eddy currents in the workpiece.

In FIG. 1, an apparatus for measuring cutting tool dullness made according to the present invention is indicated generally at 10, and comprises an eddy current proximity probe 11 that is shown only schematically, and which has leads 12 and 13 connected to one or more coils 11A. The leads 12 and 13 are connected to an adjustable frequency alternating current power source 14, that preferably generates a current in the coil or coils in the probe at a frequency in the range of at least one KHz.

The probe, for example, may be one made by Sensor Corporation of Greenwich, Conn. A current phase angle sensor indicated at 15 is connected into the circuit. The phase angle sensor 15 determines the phase of the current carried in lines 12 and 13 to the probe and through the probe 11. A comparison can be made so that any phase angle change caused by eddy currents in a part that is being sensed can be determined. As shown, a workpiece or part 20 is supported adjacent the probe 11. In this form of the invention, a machine tool 21, having a chuck 22 that has a collet 23 that holds the workpiece 20 securely for rotation. The probe can be supported on a suitable housing indicated schematically at 25 to be adjacent to but not in contact with the part. A cutting tool 26 supported on a tool holder 27 that is attached to the machine tool is engaging the workpiece 20.

The measurement of the work hardening of the surface of the workpiece 20 can be done with the workpiece removed from the collet after each part is machined, or it can also be done in real time while the parts are sequentially machined. The probe then must be adjacent to a portion of the workpiece has been machined with the tool because it is the work hardening of the surface of the workpiece after machining that gives the indication of cutting tool dullness.

Figure 2:
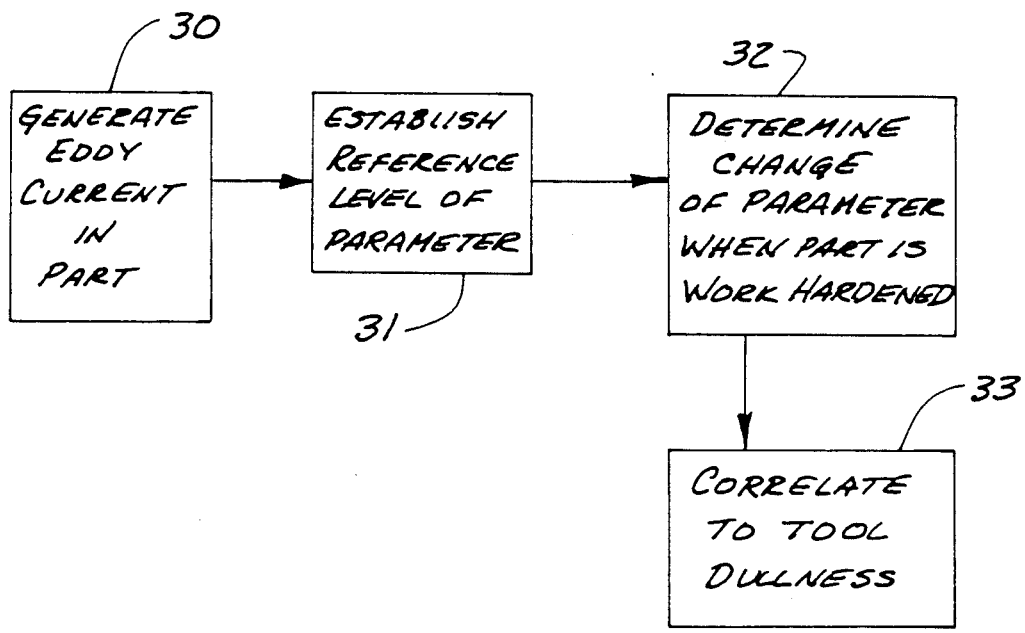
FIG. 2 is a flow diagram of a method used for determining cutting tool dullness as a function of work hardening of the workpiece.

The process is simple, as shown in FIG. 2, in that it includes a step of generating the eddy current in the part, as indicated at 30, and establish a relative reference level of the parameter to be measured that is related to eddy current generation, as shown at 31. This is dependent on the bulk properties of a workpiece that is placed adjacent the probe 11, or other eddy current generator. Next, after machining, a determination is made of the change in the parameter when the part is work hardened as indicated at 32. This is then correlated to tool dullness by previous calibration, and can be done on-line utilizing a computer that has the output of a current phase sensor fed to it, and has a program that establishes a relationship similar to the values shown on the plot in FIG. 3, for example.

Figure 3:
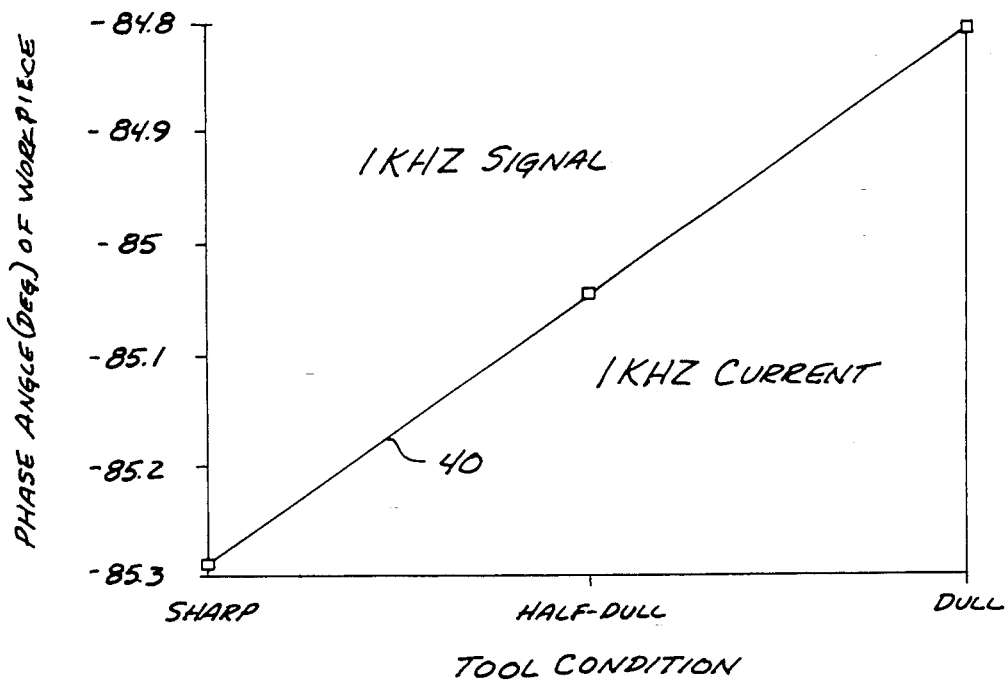
FIG. 3 is a graph indicating a plot of phase angle of current in an eddy current coil versus cutting tool dullness using a current at a frequency of about 1 KHz.
Figure 4:
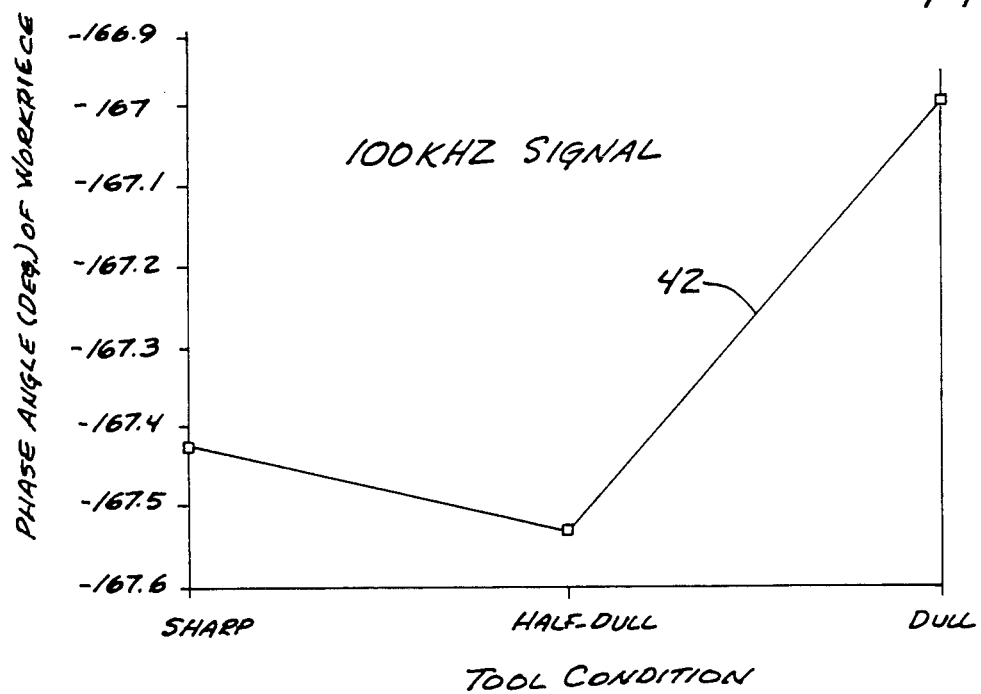
FIG. 4 is a plot of phase angle versus cutting tool dullness at a substantially higher frequency (100 KHz) to illustrate the effects of higher frequency eddy currents on measuring work hardening.

In FIG. 4, the higher frequency 100 KHz signal is shown to provide repeatable results, but not straight line results. The straight line results are desired. Frequencies in the range of 500 Hz to 25 KHz provide a generally straight line relationship. In FIG. 3, a plot is shown for cutting tool condition on the horizontal or X axis, and the phase angle of the current in the coil having a workpiece present is shown on the vertical axis or Y axis. The numbers are from actual experimental determinations, and when standard workpieces are being worked on, the reference point with a sharp tool can be the same because the workpieces are the same bulk. As shown, a straight line plot 40 is arrived at, utilizing a one KHz input current to the coil. As the tool dulls, workpieces that have been machined will be more work hardened causing a change in the eddy currents formed, which causes the phase angle shift to result. The measured phase angle becomes less negative, as shown by FIG. 3, as the tool dulls and work hardening increases. The amount of change of phase angle is adequate for determining easily a change that will correlate into cutting tool dullness using conventional phase angle measuring circuits.

FIG. 4 shows a plot 42 of the same conditions using a 304 stainless steel rod, but at 100 KHz input current. The phase angle actually becomes more negative during the first wearing of the tool, and then changes to become less negative. This relationship is more difficult to correlate on a real time basis or when individual piece parts are being examined after having been machined, so that frequency in the range of one KHz is the preferred mode, but that the frequency can range from 500 Hz to in the range of 25 KHz, for the preferred frequency range.

The eddy currents are generated with sufficient strength so that they will cause a measurable phase angle shift.

Other eddy current dependent parameters can be used, such as the measurement of the change of the magnetic field flux generated in the coil due to losses by eddy currents, but phase angle shift is a reliable, low cost, and accurate way of determining changes in the eddy current response caused by work hardening of the workpiece surface.

When a selected parameter value of the work hardening-dullness indicator signal is reached, as illustrated by the calibration plot 40, the cutting tool will be considered dull. Reaching this parameter value can be included as an audible or visual signal from the apparatus that provides a measurement of the phase angle.

Because of variations in chemistry, handling, and other conditions of the workpieces, monitoring only the change in work hardening in the surface at one frequency may not be satisfactory, and in such a case, the power supply 14 for probe can provide a multi-frequency current. By comparing the physical properties at the very top (0 to 10 micron) layer of machined surface, and the properties of a larger cross section or deeper cross section in the range of 100 to 100,000 microns, a very fast and accurate diagnosis of the change of physical properties due to tool dullness can be obtained. The lower frequency currents analyze a deeper layer.

Magnetic conductivity, thermal conductivity or acoustic conductivity are parameters that can be measured by eddy currents. If a multi frequency eddy current is generated with the power supply to the probe, the frequency in the range of 100 KHz will register changes in magnetic permeability and electrical conductivity in a 0.005 inch layer for high speed steel. This is a relatively shallow layer. With the one KHz signal, the depth of the layer that is carrying eddy currents in the piece part may be in the order of 0.05 inches. The change in properties between the two layers, such as those illustrated in FIGS. 3 and 4 at different frequencies can be correlated to tool dullness on different materials very quickly, and measuring one parameter, while comparing the changes in the parameter caused by changes in structure of the metal at different depths from the surface being worked on by the cutting tool, gives a more complete profile of work hardening and a better indication of the work hardening occurring. This then gives a more complete indication of cutting tool dullness.

Thus the units are relatively inexpensive, and can easily be utilized with known technology.

The eddy current can be generated with simple coils excited by suitable frequency currents. The workpiece could be inserted into the interior of the coil for measurement as well.

The generation of multi-frequency eddy currents can be done sequentially, so that a particular frequency can be first applied, and then subsequently a second frequency applied and the results stored and compared. In effect, if the outer surface is damaged or has a different chemistry than some other work parts, the inner or the deeper layer will also be analyzed to confirm the determination of tool dullness.

The tool can be a drill bit, end mill, a cutter for a lathe or any machine tool cutter.

Although the present invention has been described with reference to preferred embodiments, workers skilled in the art will recognize that changes may be made in form and detail without departing from the spirit and scope of the invention.

What is claimed is:

1. An apparatus for determining dullness of a tool by analyzing changes in work hardening of a surface of a workpiece machined by the tool, the apparatus comprising an eddy current generator to generate eddy currents in the workpiece positioned adjacent the surface of the workpiece after machining through which a current at a frequency above 500 Hz is passed, and measuring means connected to the eddy current generator, the measuring means providing a reference work hardening surface measurement for a known parameter of the generated eddy currents indicating an initial condition of the machining tool, and providing subsequent work hardening surface measurements of the known parameter for correlation with the reference work hardening surface measurement as the workpiece is machined by the tool, wherein changes in the measured parameter from the reference measurement correspond to eddy current changes in the workpiece and thereby correlate to tool dullness.

2. The apparatus as specified in claim 1 wherein said means to measure a parameter comprises means for measuring a phase shift in the current to the eddy current generator due to the presence of the workpiece adjacent the generator.

3. The apparatus as specified in claim 1 and means for providing a current to the eddy current generator that is in the range of 100 KHz.

4. An apparatus for determining cutting tool dullness comprising means for generating eddy currents in a workpiece which was machined by such cutting tool, means for supporting a workpiece adjacent to said means for generating eddy currents, and means connected to the eddy current generator for measuring a parameter related to the generated eddy currents which changes with surface work hardening in the workpiece before the workpiece is machined to obtain an initial work hardening reference measurement, and at least after the workpiece is machined to obtain a second work hardening measurement, and comparing the second measurement with the initial reference measurement to obtain a representation for dullness of a cutting edge of the tool machining such workpiece.

5. The apparatus as specified in claim 4 wherein said means for generating eddy currents comprises a probe positioned adjacent the workpiece, and the means for measuring a parameter comprises a phase shift member determining the shift in phase of current provided to the probe due to presence of the workpiece.

6. The apparatus as specified in claim 5 wherein the means for generating eddy currents selectively provides current at least two different frequencies.

7. A method of determining the condition of a cutting edge of a tool machining a workpiece made of a material in which eddy currents can be generated and which is work hardened by the cutting edge, the method comprising the steps of:

providing electrical energy that causes eddy currents to be generated in a workpiece to be diagnosed;

placing the workpiece in position to be affected by the eddy currents;

establishing a reference work hardening surface measurement of the workpiece for a known parameter based on the eddy currents indicating an initial condition of the cutting edge;

taking subsequent work hardening surface measurements of the known parameter as the workpiece is machined by the cutting edge;

comparing the subsequent measurements with the reference measurement; and obtaining from the comparison a representation of cutting edge dullness.

8. The method of claim 7 wherein the steps of establishing and taking subsequent work hardening measurements comprises measuring a phase angle shift of the electrical energy caused by the presence of the workpiece.

9. The method of claim 7 wherein said means for generating eddy currents comprises a probe that is placed adjacent the workpiece as the workpiece is machined.

10. The method of claim 7 included the step of providing electrical energy by a current having a frequency in the range of 1 KHz.

11. The method of claim 7 wherein the step of providing includes providing electrical energy comprising current at a first frequency and at a second frequency that causes corresponding eddy currents in the workpiece to be diagnosed; the step of establishing includes making a first reference measurement for a known parameter at the first frequency, and a second reference measurement for the known parameter at the second frequency, both reference measurements indicating an initial condition of the cutting edge; the step of taking subsequent measurements includes taking measurements of the known parameter at the first and second frequencies; and the step of comparing includes comparing the subsequent measurements with the corresponding reference measurements.

12. A method of claim 11 wherein the first and second frequencies are each between 500 Hz and 100 KHz and are different from each other.

* * * * *